United States Patent [19]

Vollweiler

[11] Patent Number: 5,150,622
[45] Date of Patent: Sep. 29, 1992

[54] VAPOR PROBE FOR SOIL GAS VAPOR SAMPLER

[76] Inventor: Arthur R. Vollweiler, 105 Harrison, American Falls, Id. 83211

[21] Appl. No.: 657,669

[22] Filed: Feb. 19, 1991

[51] Int. Cl.$^5$ .............................................. G01N 1/10
[52] U.S. Cl. .................................. 73/864.74; 175/20; 175/21
[58] Field of Search ............... 73/864.74, 863.23; 175/58, 59, 20, 21

[56] References Cited

U.S. PATENT DOCUMENTS

| | | | |
|---|---|---|---|
| 1,862,339 | 6/1932 | Highmark | 175/20 |
| 3,943,750 | 3/1976 | McLaughlin | 73/864.74 |
| 4,310,057 | 1/1982 | Brame | 73/964.74 |
| 4,335,622 | 6/1982 | Bartz | 73/864.74 |
| 4,350,051 | 9/1982 | Thompson | 73/864.74 |
| 4,452,091 | 6/1984 | Richers | 73/864.74 |
| 4,804,050 | 2/1989 | Kerfoot | 175/20 |
| 4,807,707 | 2/1989 | Handley et al. | 73/864.74 |
| 5,000,051 | 3/1991 | Bredemeier | 73/863.23 |
| 5,010,726 | 4/1991 | Lucero et al. | 73/863.23 |
| 5,035,149 | 7/1991 | Wierenga | 73/863.23 |

Primary Examiner—Hezron E. Williams
Assistant Examiner—Howard Wisnia
Attorney, Agent, or Firm—K. S. Cornaby

[57] ABSTRACT

A device for sampling gas vapor underground has a probe tip designed to be driven into the ground. The probe tip has a removable sheath that covers a tube having an enlarged conical tip with the tube having multiplicity of apertures in the tube to gather soil gas vapors through the apertures and conduct them through a flexible plastic tube attached to the probe up to the surface of the ground to be monitored. The probe has a flexible disc attached thereto above the apertures to protect the apertures from being filled with earth from above. The apertures also have a screen around them to prevent earth from entering the apertures to plug them. After the probe is in place in the earth, the removable sheath is pulled above ground, leaving the probe to gather gas samples for collection and evaluation at a collection point above ground.

5 Claims, 3 Drawing Sheets 5,150,622

VAPOR PROBE FOR SOIL GAS VAPOR SAMPLER

BACKGROUND OF THE INVENTION

For many years, there have been several devices developed to extract vapor samples from the soil.

In the past few years the need for vapor sampling has greatly increased. This need is due to the Environmental Protection Agency's (EPA's) requirements to monitor underground fuel storage tanks for leakage into the soil.

Underground fuel tanks are not limited to fuel such as gasoline, diesel or fuel oil but cover a full spectrum of tanks buried underground that contain a toxic or volatile liquid, which, if leaks occur, could contaminate the earth or leak into the aquifer.

The common method for testing the surrounding soil for leaks is to drive a fallout test probe into the ground next to a storage tank and collect a sample of vapors from the probe area through a tube extending from the probe to the surface of the ground. Typically, a metal driving tube surrounding the sampling tube is used to drive the probe into the ground.

In the prior art, there has always been a problem with dirt falling in around the vapor probe when it is in place near the tank. This creates a problem by filling the vapor inlet holes in the probe with dirt and plugging them.

It is an objective of this invention to provide a means to minimize or eliminate this problem.

SUMMARY OF THE INVENTION

The probe tip of the improvement according to the invention is conically shaped. The tip is pointed, but is machined so that the exterior circumference above the point is larger than that of the drive tubes. Probes can be made to any dimension depending on the size of drive tubes.

Just above the largest circumference of the probe, the probe is reduced to a smaller diameter. This creates a shelf for the drive tube to rest on. The probe is reduced to an even smaller diameter above this shelf. The size is maintained for a short distance of approximately ⅜"; however, this length may vary depending on the number of vapor inlet holes needed or the amount of area specified for a soil gas profile. These holes intercept a vertical cavity that extends the length of the interior of the probe and connects with the sample tube at the upper end of the probe.

Above the vapor inlet hole area, the vapor probe expands to a larger diameter. This diameter is still smaller than the diameter of the largest point on the probe. The longer circumference of the upper portion acts as an umbrella over the vapor inlet holes. This umbrella feature prevents dirt from falling in and around the vapor holes after the drive tube is removed.

Just above the umbrella portion, the diameter of the probe is greatly reduced, this diameter varies to the size of flexible plastic or Teflon tubing used for extracting vapor. The final portion on this end is a series of several cuts in the prove, and each cut is tapered. By using this feature, the flexible sample tubing can easily be pushed on, but because of the tapered cut, the tubing cannot be pulled off. This feature is important because if the probe tip cannot be inserted to a desired depth, the flexible tube can be pulled up with the drive tube; and the vapor tip can be retrieved. If the probe cannot be pulled by hand, a reverse hammer attachment can be used to drive the vapor probe out of the ground. By using a tapered cut, no wire is needed to secure the tubing to the probe.

When the probe is driven into the ground, a flexible washer preferably of Teflon or plastic material, is attached to the umbrella portion of the probe and is inserted into the drive tube. When the probe has been inserted to the proper depth, the drive tube is removed. At that time, the plastic washer unfolds and rests against the sides of the wall of the hole created after driving the probe tip into the earth to prevent soil from falling from above into the space around the vapor sample inlet holes.

This feature is very important inasmuch that after the probe has been inserted and the driving tubes have been removed, the space around the sample tube can be filled with soil. In this way, true vapor samples can be collected from the earth at the specified depth without concern for plugging the inlet holes and contaminating the sample with outside air from the ground surface.

Probes mentioned in the prior art have no means of protecting the vapor sampling holes from being plugged after the probe is in place.

The invention also provides a hammer head for driving the probe tube into the ground. The plastic sampling tube enters the head from the side to provide an unobstructed area for the hammer to hit the head directly from above. The drive head is either screwed or pinned onto the drive tube. The plastic vapor sampling tube extends inside the drive tube and attaches to the vapor probe tip. The drive head is constructed to allow the operator to unscrew the drive head from the drive tube, remove the drive head from the vapor tube and insert the end of the vapor tube into another section of drive tube.

THE DRAWINGS

FIG. 1 is a perspective of a soil vapor sampling probe in place near an underground storage tank;

FIG. 2, a side elevational view of a probe in the soil showing a removable drive tube in place;

FIG. 3, a side elevational section of the probe of the invention in place in the soil with the drive tube in place;

FIG. 4, a side elevational section of the probe of the invention shown in FIG. 3, with the driving tube removed; and FIG. 5, is a top elevational section of the probe taken along lines 5—5 of FIG. 4;

FIG. 6, a side elevational section of the driving device for driving the driving tube and vapor sampling tube into the soil.

DETAILED DESCRIPTION OF THE DRAWINGS

Figure 1:
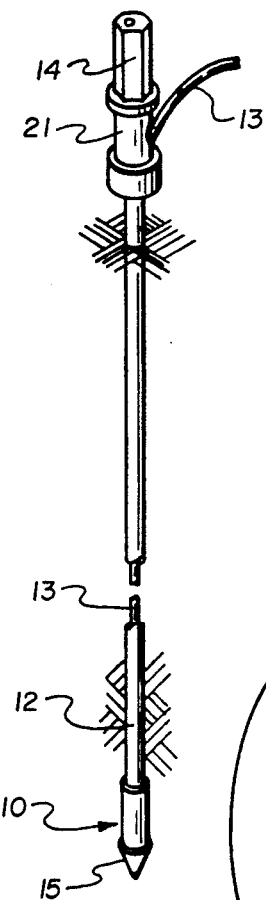
Figure 1:
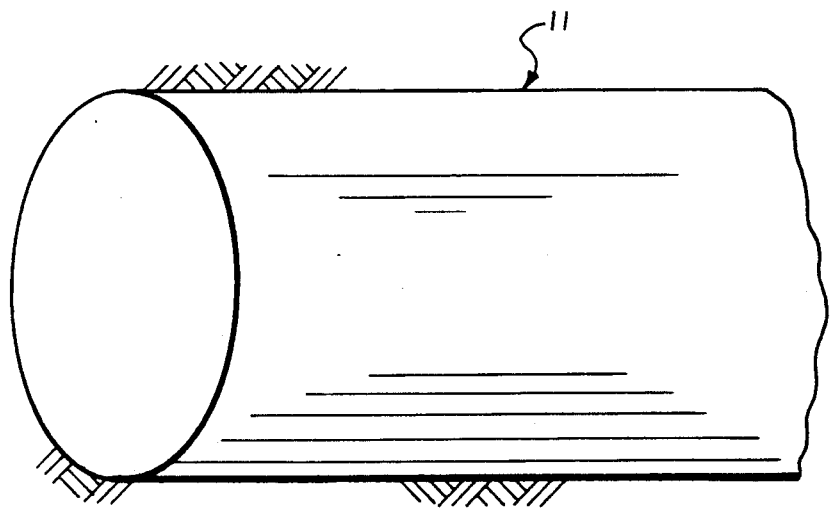
Figure 2:
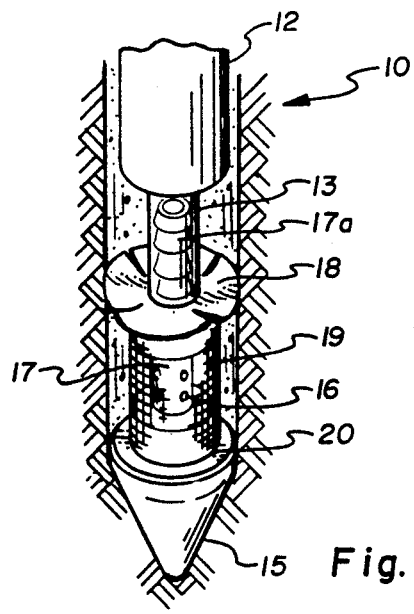

As shown in FIGS. 1 and 2, a sampling probe 10 of the invention is driven into the ground near an underground fuel storage tank 11, using a driving tube 12 encircling a flexible vapor sampling tube 13 by means of a driving hammer 14.

Figure 3:
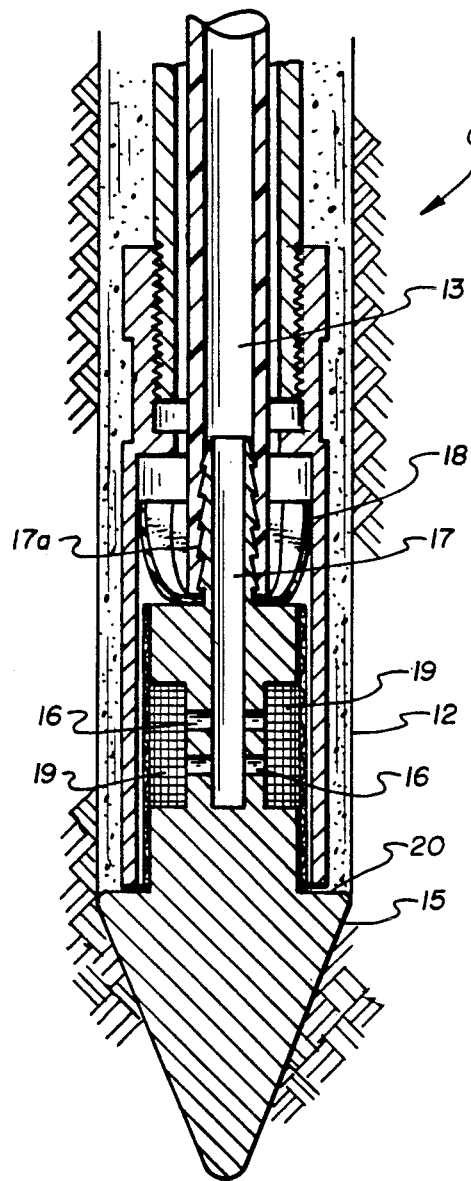
Figure 4:
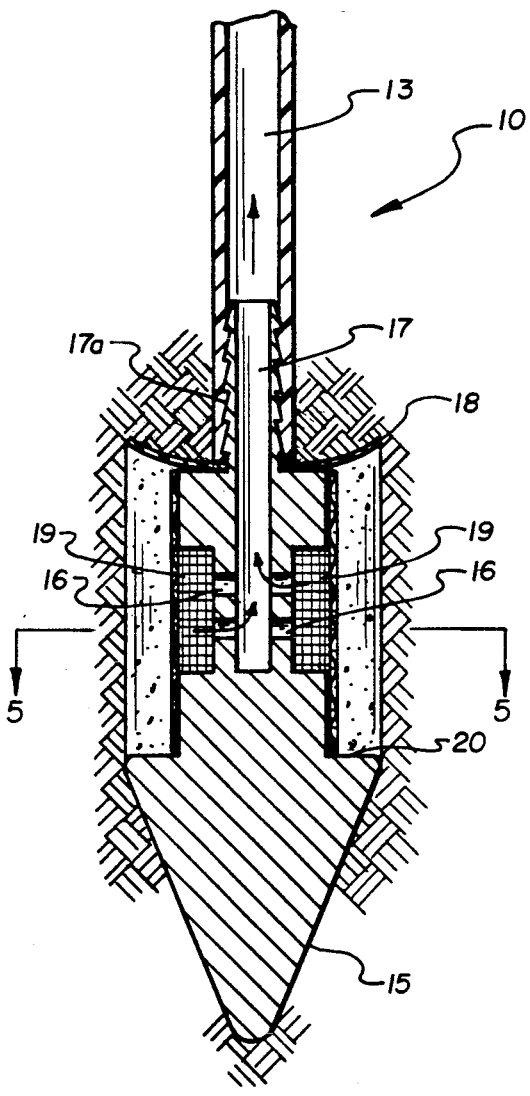
Figure 5:
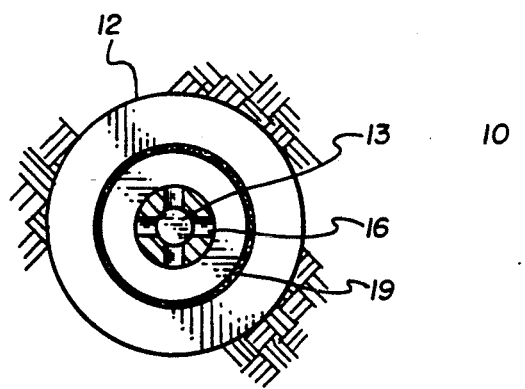

As shown in FIGS. 3, 4 and 5, the vapor probe tip 15 has a metal tube 17 that has a series of vapor inlet holes 16 with a machined tang which has a series of diagonally cut barbs 17a that allows a section of flexible tube 13 to be pushed onto the barbs on the tang 17a, but when one pulls on the tube 13, it cannot be pulled off.

A hole is drilled through the center of the metal tube 17 and meets the vapor inlet holes 16. A flexible plastic or Teflon disc 18 is installed on the metal tube 17. Disc 18 functions as an umbrella to prevent the vapor inlet holes 16 from being plugged by surrounding or falling earth. In addition, a screen 19 can be installed around vapor holes 16 to prevent earth from entering into the vapor hole 16.

To install the probe tip 15, the operator first puts the plastic or Teflon disc 18 on the vapor probe tip 15 then pushes the plastic or Teflon tube 13 onto the metal tube 17. A section of drive tube approximately 4 feet long constructed of stainless steel or high carbon steel is then inserted over the sampling tube 13. The disc 18 is then folded upwardly to fit under the drive tube 12, and drive tube 12 is placed over the rest of the vapor probe tip. Drive tube 12 rests on a machined shelf 20 on the probe tip 15. When the drive tube 12 is installed, the vapor inlet holes 16 are then protected and will not fill with dirt while the probe 10 is driven into the soil.

Figure 6:
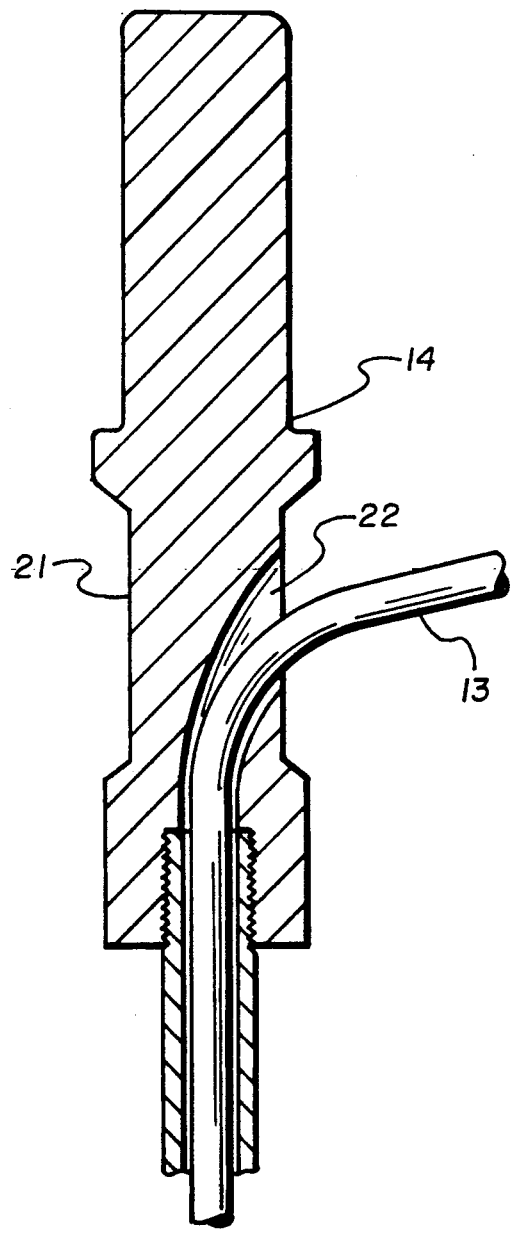

As shown in FIG. 6, the other end of the vapor sampling tube is then inserted into the drive head 14, the end of the tube 13 follows a channel 22 through the drive head 21 and exits through the side of the drive head 21. The drive head 21 is then attached to the drive tube 12. An up and down hammer attachment 14 is then secured to the drive head 21. The probe 10 can now be driven into the ground.

Not only can the up and down hammer attachment be used, but an electric rotary hammer or hydraulic system can be used to insert the tip into the ground. The drive head can be removed from the drive tube and additional drive tubes can be attached together, so the tip can be inserted to the desired depth. When the tip is at its desired depth, it can be left to obtain vapor samples by removing the drive tubes. When the tubes are removed, the plastic or Teflon disc that is on the metal tang unfolds and protects the vapor inlet holes from filling with dirt. The machined shelf on the tip also creates a dead air space around the vapor inlet holes.

After the drive tubes are removed, the Teflon or plastic sampling tube stays attached to the probe tip. Dirt is then placed around the Teflon or plastic tube at the surface of the ground. This prevents surface air from contaminating the air pocket around the probe tip. The Teflon or plastic sampling tube is then attached to a small vacuum pump or gas chromatograph, at which point vapor samples can be extracted from below the surface of the earth. The probe tip and Teflon or plastic tube are left permanently at the specific locations, so that at any time a vapor sample can be taken. This use is not limited to tanks but can be used in monitoring soil gas in landfills, pipelines and underneath houses or any buildings for Radon gas or any potentially toxic fumes or vapors.

While this invention has been described and illustrated herein with respect to preferred embodiments, it is understood that alternative embodiments and substantial equivalents are included within the scope of the invention as defined by the appended claims.

I claim:

1. A soil gas sampling probe for obtaining soil gas samples in the earth, comprising in combination:
  a. an elongate cylindrical sampling tube provided with an upper and a lower end and having a multiplicity of gas intake apertures on a surface of the tube;
  b. a conically shaped probe tip attached to the lower end of said elongate sampling tube for penetrating the earth as the probe is inserted into the earth to a predetermined depth, said tip having a circumference larger than said cylindrical tube and having a circumferential shelf therein;
  c. screening means surrounding the apertures in said cylindrical sampling tube;
  d. a flexible disc attached to the upper section of said sampling tube for preventing soil from falling downwardly into a void surrounding said sampling tube and its apertures;
  e. flexible tubing attached to the upper end of said sampling tube for transporting gas samples collected through the sampling tube upwardly to the earth's surface; and
  f. a removable rigid driving tube surrounding said cylindrical sampling tube and flexible disc for driving said sampling tube into the earth to a predetermined depth; said driving tube being adapted to rest on the circumferential shelf of said conical probe tip while the tip is driven into the earth, and to be removed when the predetermined depth is reached.

2. A soil gas sampling probe as set forth in claim 1, including a hammerable surface at the upper end of said driving tube for driving said driving tube into the earth.

3. A soil gas sampling probe to set forth in claim 1, wherein said sampling tube is constructed of rigid material.

4. A soil gas sampling probe as set forth in claim 1, wherein the flexible disc is constructed of a thermoplastic material.

5. A soil gas sampling probe as set forth in claim 1, wherein said cylindrical sampling tube has fluted retaining surfaces at its upper end to fixedly retain flexible tubing attached thereto.

* * * * *